(12) United States Patent
Santasiero

(10) Patent No.: US 8,614,184 B2
(45) Date of Patent: Dec. 24, 2013

(54) HCG FORMULATIONS FOR ACHIEVING WEIGHT LOSS

(76) Inventor: Ronald P. Santasiero, Eden, NY (US)

(*) Notice: Subject to any disclaimer, the term of this patent is extended or adjusted under 35 U.S.C. 154(b) by 332 days.

(21) Appl. No.: 12/888,051

(22) Filed: Sep. 22, 2010

(65) Prior Publication Data
US 2012/0071408 A1    Mar. 22, 2012

(51) Int. Cl.
| | | |
|---|---|---|
| *A61K 38/24* | (2006.01) | |
| *C07K 14/59* | (2006.01) | |
| *A61K 31/51* | (2006.01) | |
| *A61K 31/525* | (2006.01) | |
| *A61K 31/714* | (2006.01) | |
| *A61K 31/4415* | (2006.01) | |

(52) U.S. Cl.
USPC .......... 514/9.7; 514/10.3; 514/52; 514/251; 514/276; 514/904; 530/350; 930/110

(58) Field of Classification Search
None
See application file for complete search history.

(56) References Cited

U.S. PATENT DOCUMENTS

| | | | |
|---|---|---|---|
| 4,737,364 A * | 4/1988 | Kalogris | 424/195.15 |
| 5,428,023 A | 6/1995 | Russell-Jones et al. | |
| 5,807,832 A | 9/1998 | Russell-Jones et al. | |
| 7,605,122 B2 | 10/2009 | Tuntland | |
| 2007/0026027 A1 * | 2/2007 | Tuntland | 424/400 |
| 2008/0286254 A1 * | 11/2008 | Sakamoto et al. | 424/93.45 |
| 2009/0181883 A1 | 7/2009 | Tuntland | |

OTHER PUBLICATIONS

Schlutz et al., Journal of Nutrition, 1938; 15: 411-427.*
Briggs and Besson, J Anim Sci, 1951; 10: 820-827.*
Asher et al., The American Journal of Clinical Nutrition, 1973; 26: 211-218.*
AT Simeons, Lancet, 1954; 267: 946-947.*

* cited by examiner

*Primary Examiner* — Bridget E Bunner
*Assistant Examiner* — Christina Borgeest
(74) *Attorney, Agent, or Firm* — Vincent G. LoTempio; Kloss, Stenger & LoTempio; David T. Stephenson

(57) ABSTRACT

A formulation of human chorionic gonadotropin (HCG) for promoting weight loss comprising reconstituted HCG in an amount sufficient to promote weight loss; at least one vitamin selected from the group consisting of: vitamin B1, vitamin B2, vitamin B3, vitamin B5, vitamin B6, vitamin B7, vitamin B9, and vitamin B12; and at least one dietary supplement selected from the group consisting of: an amino acid, inositol, choline chloride, and L-carnitine.

3 Claims, No Drawings

HCG FORMULATIONS FOR ACHIEVING WEIGHT LOSS

FIELD OF THE INVENTION

The present disclosure relates generally to a formulation for achieving weight loss and more particularly to formulations containing human chorionic gonadotropin with additional dietary supplements, and even more particularly to formulations containing human chorionic gonadotropin with additional dietary supplements for use in a low calorie diet regimen.

BACKGROUND OF THE INVENTION

The human chorionic gonadotropin (HCG) weight loss protocol was originally developed by Dr. A. T. Simeons in the late 1940's. Dr. Simeons postulated that obesity was due to humans eating excessive calories for a prolonged period of time, causing the fat storage center of the brain to store the excess calories in a deep fat reserve. Dr. Simeons conducted research after World War II on concentration camp victims, and found that 85% became obese within six months of being released from captivity, even if they were not obese before. He postulated this was due to the fat storage center in the brain being open to its storage mode once the diet of these people contained more calories than the body was consuming in captivity.

Dr. Simeons theorized that the deep fat reserve was only broken down after prolonged severe calorie restriction, or after using HCG with calorie restriction. HCG, with calorie restriction, could result in a weight loss of up to 35 lbs. in six weeks, if the protocol was strictly followed. If the weight loss is maintained for approximately three to four weeks post HCG and diet, the weight loss is permanent in most people, due to a re-setting of the fat storage mechanism in the brain.

Dr. Simeons refined the protocol in Rome, Italy for 20 years after he started using the original protocol. Dr. Simeons postulated the use of low dose HCG (125 units intramuscularly) could enhance weight loss when a low calorie (500 calories per day) diet was followed. In his original work, and in all protocols since, the use of supplemental vitamins is discouraged, because it is felt the fat breakdown from the use of HCG releases vitamins and nutrients stored in the fat.

A double-blind study performed in 1973 by Asher and Harper supports the claims of Dr. Simeons. Asher, W L, Harper, H W. (1973) Effect of human chorionic gonadotrophin on weight loss, hunger, and feeling of well-being. *The American Journal of Clinical Nutrition*, 26, pp 211-218. The study began with subjects who were all treated for obesity using the Simeons protocol, but half were treated with HCG and half with an identical appearing placebo. Subjects were to be given a daily injection six days per week for a total of 36 injections, unless they reached their goal weight before completing six weeks of treatment. In the control group (placebo), 65% completed at least 30 injections and lost a mean of about 11 lbs. In the study group (HCG), 85% completed at least 30 injections and lost a mean of about 20 lbs. Little or no hunger was reported by about 50% of the control group while about 80% of the HCG group reported little or no hunger.

U.S. Pat. Nos. 5,428,023 (Russell-Jones, et al.) and 5,807,832 (Russell-Jones, et al.) disclose an orally administered composition ('023) and a method of treating a patient using that composition ('832). The composition comprises a hormone (HCG) covalently linked to vitamin B12 or a B12 analog. The B12 carrier molecule is capable of binding an intrinsic factor for uptake within the small intestine. A linking agent links the hormone to B12 molecule through the carboxyl group of an acid-hydrolyzed propionamide side chain. The method simply entails providing the above composition to a patient for oral administration. The formulation and method of the '023 and '832 patents possess distinct drawbacks. For one, the patents chemically bind HCG to another molecule using a linking agent. This binding requires additional manufacturing steps increasing the cost of production while also increasing the chances of product contamination. Moreover, the HCG is physically modified which may adversely affect its efficacy. Additionally, these patents do not describe or suggest the use of other vitamins or dietary supplements for use with HCG in a low calorie diet.

U.S. Pat. No. 7,605,122 (Tuntland) and United States patent application 2009/0181883 (Tuntland), describe a sublingual composition comprising human chorionic gonadotropin maintained at pH 7-8 using a sodium bicarbonate buffer along with glycerin and ethanol. The composition was developed to be used in a very low calorie diet protocol. The composition may further contain an absorption rate enhancer such as mineral oil or corn oil. Patent '122 describes using diet suppressants and/or potassium supplements during the diet. However, the suppressants and potassium supplements do not satisfy the underlying condition which causes dieters to continue to feel hunger—namely lack of nutrients. The additives in the formulations posited by patent '122 merely mask the symptoms of hunger and do not provide the nutrients needed by the body—particularly when on a low calorie diet.

Therefore, it is clear that a long felt need exists for a formulation containing HCG for use in a low calorie diet which satisfies a dieter's hunger response. If the protocol is used properly, the HCG should circulate enough calories, vitamins, and nutrients from fat breakdown to eliminate or greatly minimize hunger. Since Dr. Simeons did his work over 50 years ago, when eating habits were much different, a body's stored fat contained more nutrients than the fat stored in people today. Today's vegetables and fruits contain far fewer nutrients than decades ago. In the 1950's most nutrition was from fresh fruits and vegetables which were allowed to ripen naturally. This is not the case today where vegetables are picked before fully ripe. Also, many of the stored fat calories today come from prepared or junk foods, which have little or no nutritional value. Therefore, it is possible that the breakdown of fat today releases very low levels of vitamins and minerals. It has been found that approximately 20% of people on a low calorie diet with an HCG regimen still experience hunger. The current disclosure postulates that the hunger, while on HCG, is due to the brain perceiving a need for some vitamins and nutrients not found in our fat today. It has been observed that if certain vitamins and nutrients are added to the HCG, the percent of people who get hungry while on the protocol drops from about 20% to about 5%. The formulation of the present disclosure comprises HCG, B-complex vitamins, and select amino acids and other dietary supplements.

SUMMARY OF THE INVENTION

It is a general object of the present disclosure to provide a formulation containing human chorionic gonadotropin and dietary supplements for use in low calorie diets.

It is a further object of the present disclosure to provide a formulation containing human chorionic gonadotropin and dietary supplements wherein the dietary supplements include at least one of an individual B vitamin, vitamin B-complex, and at least one amino acid.

It is yet a further object of the present disclosure to provide a formulation containing human chorionic gonadotropic and dietary supplements for oral administration.

It is yet a further object of the present disclosure to provide a formulation containing human chorionic gonadotropic and dietary supplements for subcutaneous administration.

It is yet a further object of the present disclosure to provide a formulation containing human chorionic gonadotropic and dietary supplements for trans-dermal administration.

These and other objects, features and advantages of the present disclosure will become readily apparent to those having ordinary skill in the art upon a reading of the following detailed description in view of the appended claims.

DETAILED DESCRIPTION OF THE PREFERRED EMBODIMENT

A human body's deep fat reserve is broken down after prolonged severe calorie restriction, or after using HCG with calorie restriction. Protocol participants cannot be insulin dependent diabetics nor have active cancer. Protocol participants must have a recent complete blood count test (CBC) and metabolic profile. Protocol participants have to keep a one week log of everything they eat prior to inclusion within the HCG protocol. The diet does not include alcohol. Protocol participants that meet these requirements are candidates for the initial counseling session.

The counseling session selects protocol participants through a psychological screen to determine if there are any issues which would prevent a protocol participant from following the diet. Issues such as severe carbohydrate craving, inability to cook, or not having anyone to cook for the protocol participant would eliminate a potential participant from participating in the diet. Protocol participants are informed that in order to lose weight with this program, they must adapt their lifestyle as described herein to maintain the weight loss. These changes include monitoring their weight, exercising, following good nutrition, and caloric restriction if necessary. Also, there is a discussion concerning what foods are allowed and not allowed, cooking methods, suggested recipes, and tips to help cope with different aspects of the diet.

After the counseling session, protocol participants meet with the physician for a history and physical examination. Any problem medications are discussed, as well as any adjustments to those medications. The same discussion is conducted concerning dietary supplements. Protocol participants cannot have serious active disease during the initiation of the diet. The medical aspects of the diet are discussed and any questions are answered. The physician calculates and pre-measures the dose of the enhanced HCG as described in the embodiments of the present disclosure.

In one embodiment, the enhanced HCG is administered via subcutaneous injection. Using subcutaneous injection, the dose is generally between 200 and 300 units of HCG depending on participants' weight and other factors, such as carbohydrate cravings and previous eating habits. The protocol participant is shown the self-injection technique and they then demonstrate it to the physician. If the participant is unable to self-inject, another party is shown the technique or the protocol participant comes to the office daily for the injections. Preferably, the injections are subcutaneous using a 1 cc syringe with a ½ inch 27 gauge needle. Before leaving the physician's office, twenty three pre-loaded syringes are given to the protocol participant.

During the first week after starting the diet, close communication is maintained with the protocol participant, either through electronic mail (email), text messaging, or more preferably telephone communication. The protocol participant must maintain a diet of 500 calories for the duration of the diet. Any problems with weight plateaus, hunger, headaches or other symptoms are discussed during the communications. Protocol participants are encouraged to keep close contact with the physician during phase one (start of diet through week three or six).

After three or six weeks, depending on the amount of weight loss desired and participant motivation, protocol participants enter phase two of the diet. During this phase, the participants maintain weight while increasing calorie intake. The rate and amount of calorie increase is determined by the physician during an office visit near the end of phase one. Protocol participants must avoid all white starches, such as but not limited to breads, baked goods, pasta, and potatoes, during phase two. They must eat nutritionally dense food, and avoid processed foods during phase two. If participants gain more than two pounds over their final weight after phase one, they must diet to that weight again. Over 80% of protocol participants maintain weight loss for at least six months if they follow this protocol using the enhanced HCG composition of the present disclosure. Participants cannot undergo another course of the diet with enhanced HCG for at least six weeks after completing phase one.

HCG with calorie restriction could result in a weight loss of up to 35 lbs. in six weeks if the protocol was strictly followed. If the weight loss is maintained for approximately three to four weeks post HCG and diet, the weight loss is permanent in most people due to a re-setting of the fat storage mechanism in the brain.

In Dr. Simeons' original work, and in the protocols since, the use of supplemental vitamins is discouraged because it is felt that the fat breakdown from the use of HCG released vitamins and nutrients stored in the fat. Since Dr. Simeons did his work over 50 years ago, when eating habits were much different, the fat contained more nutrients than the fat in people today. Today's vegetables and fruits contain far fewer nutrients than in the 1950's when fresh fruits and vegetables were allowed to ripen naturally. Also, many of the stored fat calories today come from prepared or junk foods, which have little or no nutritional value. Therefore, the breakdown of fat today releases lower levels of vitamins and minerals than fat breakdown during the 1950's.

If the low calorie protocol is used properly, the HCG should circulate enough calories, vitamins, and nutrients from fat breakdown to eliminate or greatly minimize hunger. Nevertheless, as illustrated by the 1973 Asher and Harper study, approximately 20% of people using the protocol of Dr. Simeons still experience hunger. The experienced hunger while on the HCG protocol is due to the brain perceiving a need for vitamins and nutrients not found in our fat today. Going against current teachings and adding vitamins and nutrients to the HCG protocol, the percentage of people who experience hunger using the enhanced protocol drops from about 20% to about 5%. Currently over 150 people have been treated using the HCG protocol while over eighty have been treated using the enhanced formula having added vitamins and other nutritional supplements. Experience and observation shows about 80% of the patients treated without the enhanced formula experienced little or no hunger while about 95% of those treated with the enhanced formulation experienced little or no hunger. Thus, the enhanced formulation containing the vitamins and supplements improves the sensation of not having hunger by approximately 15%.

Embodiments of the present disclosure provide formulations of HCG combined with additional dietary nutrients. Current protocols using HCG with low calorie diets do not provide supplemental nutrients to the dieters. Many dieters describe feelings of hunger when on a low calorie diet and are therefore more likely to deviate from the strict diet regimen. Straying from the protocol greatly impacts the long-term effectiveness of the diet as the fat-storage mechanism in the brain is not properly reset. Proper reconditioning of the fat-storage mechanism of the brain is crucial for dieters to realize the full benefits of following a low calorie diet protocol. Not only do current protocols fail to provide additional dietary nutrients, it is further thought that the addition of dietary supplements may do more harm than good during the diet protocol.

One embodiment of a formulation of the present disclosure comprises HCG along with vitamin B-complex vitamins and select amino acids and other dietary supplements. In a preferred embodiment 10,000 USP units of HCG is reconstituted using 10 mL of bacteriostatic water, to which is added 10 mL of a mixture comprising 100 to 400 mg thiamine (vitamin B1), 100 to 400 mg niacinamide (vitamin B3), 2 to 8 mg riboflavin (vitamin B2), 2 to 8 mg pyridoxine (vitamin B6), 2 to 8 mg dexpanthenol (vitamin B5), 1 to 4 mg vitamin B-12, 50 to 100 mg methionine, 100 to 300 mg inositol, 100 to 300 mg choline chloride, and 250 to 750 mg L-carnitine. More preferably, the mixture comprises 200 mg thiamine (vitamin B1), 200 mg niacinamide (vitamin B3), 4 mg riboflavin (vitamin B2), 4 mg pyridoxine (vitamin B6), 4 mg dexpanthenol (vitamin B5), 2 mg vitamin B-12, 75 mg methionine, 150 mg inositol, 150 mg choline chloride, and 500 mg L-carnitine.

The mixture of HCG and the supplement solution is then injected subcutaneously or intramuscularly at a dose of about 0.2 ml to about 0.35 ml depending on weight of the patient or individual clinical response. In alternative embodiments, the mixture is administered either orally or trans-dermally. Oral administration is achieved by administering a liquid dosage to the patient. The formulation may be administered as reconstituted, or an additional component may be added to facilitate ease of use or absorption. Such additional components include, but are not limited to glycerin, mineral oil, corn oil, and the like. However, additional modes of oral administration include, but are not limited to, a spray, capsule, lozenge, or tablet. Means of trans-dermal administration include the use of a patch or addition of an absorptive compound to the formulation to promote rapid absorption through the skin. Examples of an absorptive compound include ethanol, polyhydric alcohols such as propylene glycol and polyethylene glycol and the like, and non-toxic oils such as olive oil or lanolin.

An additional embodiment of a formulation of the present disclosure comprises HCG combined with additional nutrients selected from vitamin B-complex vitamins, select amino acids, and other dietary supplements. More specifically, HCG is combined with nutrients selected from thiamine (vitamin B1), niacinamide (vitamin B3), riboflavin (vitamin B2), pyridoxine (vitamin B6), dexpanthenol (vitamin B5), vitamin B-12, methionine, inositol, choline chloride, L-carnitine, folic acid (vitamin B9), biotin (vitamin B7). Selected nutrients are added in the following ranges: 100 to 400 mg thiamine (vitamin B1), 100 to 400 mg niacinamide (vitamin B3), 2 to 8 mg riboflavin (vitamin B2), 2 to 8 mg pyridoxine (vitamin B6), 2 to 8 mg dexpanthenol (vitamin B5), 1 to 4 mg vitamin B-12, 50 to 100 mg methionine, 100 to 300 mg inositol, 100 to 300 mg choline chloride, 250 to 750 mg L-carnitine, 0.4 to 1.0 mg folic acid (vitamin B9), 0.1 to 1.0 mg biotin (vitamin B7); and more preferably at 200 mg thiamine (vitamin B1), 200 mg niacinamide (vitamin B3), 4 mg riboflavin (vitamin B2), 4 mg pyridoxine (vitamin B6), 4 mg dexpanthenol (vitamin B5), 2 mg vitamin B-12, 75 mg methionine, 150 mg inositol, 150 mg choline chloride, and 500 mg L-carnitine, 0.8 mg folic acid (vitamin B9), 0.5 mg biotin (vitamin B7).

Although the disclosure has been described with reference to certain preferred embodiments, it will be appreciated by those skilled in the art that modifications and variations may be made without departing from the spirit and scope of the disclosure. It should be understood that applicant does not intend to be limited to the particular details described above.

What is claimed is:

1. A formulation of human chorionic gonadotropin (HCG) for promoting weight loss consisting of:
    reconstituted HCG in an amount sufficient to promote weight loss;
    at least one vitamin selected from the group consisting of: vitamin B1, vitamin B2, vitamin B3, vitamin B5, vitamin B6, vitamin B7, vitamin B9, and vitamin B12; and
    at least one dietary supplement selected from the group consisting of: an amino acid, inositol, choline chloride, and L-carnitine.

2. The formulation of claim 1, wherein said amino acid is methionine.

3. A formulation of human chorionic gonadotropin (HCG) for promoting weight loss consisting of reconstituted HCG in an amount sufficient to promote weight loss, vitamin B1, vitamin B2, vitamin B3, vitamin B5, vitamin B6, and vitamin B12, methionine, inositol, choline chloride, and L-carnitine.

* * * * *